(12) United States Patent
Modlin et al.

(10) Patent No.: US 7,459,439 B2
(45) Date of Patent: Dec. 2, 2008

(54) GRANULYSIN PEPTIDES AND METHODS OF USE THEREOF

(75) Inventors: Robert L. Modlin, Los Angeles, CA (US); Jenny J. Kim, Pacific Palisades, CA (US); Daniel H. Anderson, Los Angeles, CA (US); David S. Eisenberg, Los Angeles, CA (US); Richard L. Gallo, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 186 days.

(21) Appl. No.: 11/304,911

(22) Filed: Dec. 14, 2005

(65) Prior Publication Data

US 2006/0128623 A1 Jun. 15, 2006

Related U.S. Application Data

(63) Continuation-in-part of application No. PCT/US2004/029586, filed on Sep. 9, 2004.

(60) Provisional application No. 60/502,382, filed on Sep. 12, 2003, provisional application No. 60/554,781, filed on Mar. 18, 2004.

(51) Int. Cl.
 *A61K 38/00* (2006.01)
(52) U.S. Cl. ........................................ 514/12
(58) Field of Classification Search ........................ None
 See application file for complete search history.

(56) References Cited

U.S. PATENT DOCUMENTS

| 4,994,369 | A | 2/1991 | Krensky | |
|---|---|---|---|---|
| 6,485,928 | B2 * | 11/2002 | Stenger et al. | 435/32 |
| 2002/0044927 | A1 * | 4/2002 | Stenger et al. | 424/94.1 |

OTHER PUBLICATIONS

Simpson, "Antibiotics in acne: time for a rethink," British Journal of Dermatology (2001): 144: 225-228.*
Anderson et al., Granulysin crystal structure and a structure-derived lytic mechanism, (2003), J Mol Biol., 325(2):355-65.
Bender et al., *Pseudomonas syringae* Phytotoxins: Mode of Action, Regulation, and Biosynthesis by Peptide and Polyketide Synthetases, (1999), Microbiology and Molecular Biology Reviews, Jun. 1999, 63(2): 266-292.
Donlon et al., Localization of the human T lymphocyte activation gene 519 (D2S69E) to chromosome 2p12—q11, (1990), Cytogenet. Cell Genet., 53:230-231.
Ernst et al., Granulysin, a T Cell Product, Kills Bacteria by Altering Membrane Permeability, (2000), J. Immunol., 165:7102-7108.
Jongstra et al., The isolation and sequence of a novel gene from a human functional T cell line (1987), J. Exp. Med., 165:601-614.
Jones et al., Antimicrobial Activity and Spectrum of LY146032, a Lipopeptide Antibiotic, Including Susceptibility Testing Recommendations, (1987), Antimicrob Agents Chemother., 31(4):625-9.
Kandimalla et al., Effect of fatty acids on the permeation of melatonin across rat and pig skin in-vitro and on the transepidermal water loss in rats in-vivo, (1999), J Pharm Pharmacol., 51(7):783-90.
Kumar et al., Granulysin: a novel antimicrobial, (2001), Expert Opin Investig Drugs, 10(2):321-9.
Manning et al., Genomic structure and alternative splicing of 519, a gene expressed late after T cell activation, (1992), J. Immunol., 148:4036-4042.
Ofek et al., Antibacterial synergism of polymyxin B nonapeptide and hydrophobic antibiotics in experimental gram-negative infections in mice, (1994), Antimicrobial Agents and Chemotherapy, 38(2): 374-377.
Setoh et al., Improvement of transdermal delivery of tetragastrin by lipophilic modification with fatty acids, (1995), J Pharm Pharmacol., 47(10):808-11.
Stenger et al., An antimicrobial activity of cytolytic T cells mediated by granulysin, (1998) Science 282(5386):121-5.
Veuillez et al., Synthesis and characterization of an acylated dipeptide (Myr-Trp-Leu) with modified transmucosal transport properties, (1999), Eur J Pharm Biopharm., 48(1):21-6.
Wakabayashi et al., N-Acylated and D enantiomer derivatives of a nonamer core peptide of lactoferricin B showing improved antimicrobial activity, (1999), Antimicrobial Agents and Chemotherapy, 43(5): 1267-1269.
Wan et al., Improving pharmacokinetic properties of adrenocorticotropin by site-specific lipid modification, (2003), J Pharm Sci., 92(9):1882-92.
Wang et al., Bactericidal and Tumoricidal Activities of Synthetic Peptides Derived from Granulysin, (2000), J Immunol., 165(3):1486-90.
Yamamoto et al., Enhanced transdermal delivery of phenylalanylglycine by chemical modification with various fatty acids, (2003), Int J Pharm., 250(1):119-28.

* cited by examiner

*Primary Examiner*—Anish Gupta
*Assistant Examiner*—Thomas S Heard
(74) *Attorney, Agent, or Firm*—Bozicevic, Field & Francis LLP; Pamela J. Sherwood (57) ABSTRACT

Granulysin peptides are small antimicrobial agents with potent activity against bacteria and inflammation. A pharmaceutical composition comprising granulysin peptides as an active agent is administered therapeutically to a patient suffering from a microbial infection.

2 Claims, 4 Drawing Sheets

SEQUENCE LISTING

<160> NUMBER OF SEQ ID NOS: 2

<210> SEQ ID NO 1
<211> LENGTH: 74
<212> TYPE: PRT
<213> ORGANISM: H. sapiens

<400> SEQUENCE: 1

Gly Arg Asp Tyr Arg Thr Cys Leu Thr Ile Val Gln Lys Leu Lys Lys
 1               5                  10                  15

Met Val Asp Lys Pro Thr Gln Arg Ser Val Ser Asn Ala Ala Thr Arg
            20                  25                  30

Val Cys Arg Thr Gly Arg Ser Arg Trp Arg Asp Val Cys Arg Asn Phe
        35                  40                  45

Met Arg Arg Tyr Gln Ser Arg Val Ile Gln Gly Leu Val Ala Gly Glu
    50                  55                  60

Thr Ala Gln Gln Ile Cys Glu Asp Leu Arg
65                  70

<210> SEQ ID NO 2
<211> LENGTH: 20
<212> TYPE: PRT
<213> ORGANISM: H. sapiens

<400> SEQUENCE: 2

Thr Arg Val Cys Arg Thr Gly Arg Ser Arg Trp Arg Asp Val Cys Arg
 1               5                  10                  15

Asn Phe Met Arg
            20

GRANULYSIN PEPTIDES AND METHODS OF USE THEREOF

STATEMENT AS TO FEDERALLY SPONSORED RESEARCH

This invention was made with government support under grant number K08 AR48551-01 awarded by the National Institutes of Health. The government has certain rights in the invention.

INTRODUCTION

1. Background

Proteins present in cytoplasmic granules, including the pore-forming protein perforin, and a family of serine proteases called granzymes, have been implicated in granule mediated cytolysis. One of the proteins present in granules is the late T cell activation marker, granulysin. Granulysin is a 9 kDa arginine-rich protein, and is a member of a larger group of proteins, referred to as saposin-like proteins (sphingolipid activator protein like protein, SAPLIP). This family has been conserved for almost a billion years, from amoebas to humans. A subset of SAPLIP family members have antimicrobial activity. This subset includes NK-lysin, and amoebapores (which are used by amoebas to kill bacterial prey).

Granulysin is cytolytic against microbes and tumors. The crystal structure (see Anderson et al. (2003) J Mol Biol. 325(2):355-65), suggests a mechanism for lysis of membranes. The five-helical bundle of granulysin resembles other "saposin folds". Positive charges distribute in a ring around the granulysin molecule, and one face has net positive charge. Sulfate ions bind near the segment of the molecule identified as most membrane-lytic and of highest hydrophobic moment. The ion locations may indicate granulysin's orientation of initial approach towards the membrane. The crystal packing reveals one way to pack a sheet of granulysin molecules at the cell surface for a concerted lysis effort. The energy of binding granulysin charges to the bacterial membrane could drive the subsequent lytic processes. The loosely packed core facilitates a hinge or scissors motion towards exposure of hydrophobic surface that is proposed to tunnel the granulysin into the fracturing target membrane.

By electron microscopy, granulysin has been shown to trigger fluid accumulation in the periplasm of *M. tuberculosis*, consistent with osmotic perturbation. These data suggest that the ability of granulysin to kill microbial pathogens is dependent on direct interaction with the microbial cell wall and/or membrane, leading to increased permeability and lysis.

Experiments have been performed (see Ernst et al. (2000) J. Immunol. 165:7102-7108) to correlate the structure and function of granulysin using biophysical approaches. Synthetic peptides of granulysin conforming to a putative helix-loop-helix motif (aa 1-35, 36-70, and 31-50) were shown to retain 50-80% of anti-bacterial activity, whereas those peptides without this predicted structure (aa 1-20, 16-35, 46-65, 61-80) had <20% activity. The structural model also predicts that the α helices are amphipathic, including 15 positively charged amino acids: 12 arginine (16%) and three lysine residues. Chemical modification of the arginine residues caused complete inhibition of the antimicrobial effects of granulysin; however, modification of the lysine residues did not inhibit the antimicrobial activity. Granulysin altered bacterial membranes by increasing their permeability, inducing lesions on the surface of bacteria and separation of the cell wall and membranes from the cytoplasm. These data suggest that the ability of granulysin to kill microbial pathogens is dependent on interactions with the microbial cell wall or membrane leading to increased permeability and osmotic lysis.

There is a clinical need for novel antimicrobial agents that have low toxicity against mammalian cells. The present invention addresses this need.

2. Relevant Literature

U.S. Pat. No. 4,994,369 discloses the nucleotide and predicted amino acid sequence of the "519" protein, which was subsequently named granulysin. The sequences of granulysin variants may be accessed from the Genbank and EMBL databases, with the accession number X05044 for the mRNA sequence of 519; EMBL accession X05044 for the encoded protein; and EMBL: locus HSNKG5, accession X54101 for the NKG5 splice variant.

The sequence and structure of the granulysin gene is discussed in Jongstra et al. (1987) J. Exp. Med. 165:601-614; Donlon et al. (1990) Cytogenet. Cell Genet. 53:230-231; and Manning et al. (1992) J. Immunol. 148:4036-4042.

The use of granulysin as an antimicrobial agent may be found in U.S. Pat. No. 6,485,928, issued Nov. 26, 2002. The activity of granulysin and derivative peptides is discussed, for example, by Stenger et al. (1998) Science 282(5386):121-5; Wang et al. (2000) J Immunol. 165(3):1486-90; and Kumar et al. (2001) Expert Opin Investig Drugs 10(2):321-9.

Fragments of granulysin are described by Wang et al. (2000) J. Immunology 165:1486-1490. Ernst et al. (2000) J. Immunology 165:7102-7108 teach active granulysin peptides comprising a helix-loop-helix motif. These references are herein specifically incorporated by reference for the disclosure of granulysin peptides.

Acylated anti-microbial proteins are described by Jones et al. (1987) Antimicrob Agents Chemother. 31 (4):625-9); Ofek et al. (1994) Antimicrobial Agents and Chemotherapy 374-377, Vol 38, No.2; Bender et al. (1999) Microbiology and Molecular Biology Reviews, June 1999, p. 266-292, Vol. 63, No. 2. These references are herein specifically incorporated by reference for the disclosure of acylated anti-microbial peptides.

Wakabayashi et al. (1999) Antimicrobial Agents and Chemotherapy p.1267-1269, Vol.43, No. 5; Yamamoto et al. (2003) Int J Pharm. 250(1):119-28; Veuillez et al. (1999) Eur J Pharm Biopharm. 48(1):21-6; Setoh et al (1995) J Pharm Pharmacol. 47(10):808-11; Kandimalla et al. (1999) J Pharm Pharmacol. 51 (7):783-90; Wan et al. (2003) J Pharm Sci. 92(9):1882-92 describe modification of peptide with lipophilic moieties, including acyl groups. These references are herein specifically incorporated by reference for the disclosure of acylated peptides.

SUMMARY OF THE INVENTION

Methods and compositions are provided for the use of granulysin peptides as an antimicrobial agent. Peptides of granulysin are also shown to have anti-inflammatory activity. Of particular interest is the use of granulysin to treat cutaneous infection, for example as therapy against Propionibacterium acnes. In some embodiments of the invention, the granulysin peptide is modified to increase hydrophobicity.

In one embodiment of the invention, the granulysin peptide contains an α-helix loop α-helix structure. Peptides of interest having such a structure include peptides of at least about 10 amino acids in length, falling within the sequence of residues 31-50 of the granulysin protein. The peptide may be modified, particularly at residue 44, to increase hydrophobicity.

Granulysin peptides are small antimicrobial agents with potent activity against bacteria. Methods are provided for the use of granulysin protein as an antimicrobial agent. A pharmaceutical composition comprising granulysin as an active agent is administered to a patient suffering from a microbial infection, particularly bacterial infections, for example infections of the skin. The protein is also effective at killing a variety of microbial organisms in vitro. Granulysin peptides may be administered alone, or in combination with other bacteriocidal agents, e.g. perforin, antibiotics, etc.

DESCRIPTION OF THE SPECIFIC EMBODIMENTS

Novel compositions and methods are provided for the use of granulysin fragments and granulysin analogs, herein referred to as granulysin peptides, as therapeutic and/or prophylactic agents. Fragments of interest are peptides derived from a granulysin sequence, of at least about 10 amino acids in length, which comprise an α-helix turn α-helix structure, and derivatives thereof. Derivatives of interest comprise an amino acid substitution in at least one position, which increases the hydrophobicity of the peptide, and may further comprise a substitution of cysteine residues. These peptides are effective at killing a variety of microbial organisms, including microbes responsible for cutaneous infections. The peptides are also shown to be useful as anti-inflammatory agents. Granulysin peptides are administered alone or in combination with other active agents to a patient suffering from an infection or inflammation in a dose and for a period of time sufficient to reduce the patient population of pathogenic microbes or inflammation.

Specific treatments of interest include, without limitation: using granulysin fragments or a granulysin analog to treat infection, for example: aerosol administration to the lungs of patients with cystic fibrosis to combat infection or forestall the emergence of resistance to other inhaled antibiotics; instillation into the urinary bladder of patients with indwelling catheters to prevent infection; application to the skin of patients with serious burns; application to patients for the treatment of acne; ophthalmic instillation, directly or in ophthalmic solutions, to treat or prevent infection; intravaginal application to treat bacterial vaginosis and/or prevent sexually transmitted disease. Granulysins may find particular benefit in patients suffering from infection and inflammation; as can occur in a variety of situations. The granulysins may be administered alone or in conjunction with other anti-microbial and/or anti-inflammatory therapy.

Granulysin Compositions

For use in the subject methods, granulysin peptides comprising an α-helix turn α-helix structure, of at least about 10 amino acids, usually at least about 12 amino acids, at least about 15 amino acids, and which may include residues 1-35, 36-70; 42-51; and 31-50 of human granulysin, and modifications thereof. A combination of one or more forms may be used.

The granulysin sequence may be from any mammalian or avian species, e.g. primate sp., particularly humans; rodents, including mice, rats and hamsters; rabbits; equines, bovines, canines, felines; etc. Of particular interest are the human proteins. Generally, for in vivo use the granulysin sequence will have the same species of origin as the animal host. For in vitro use, any convenient species having high activity against the microbe being treated may be used.

The naturally occurring form of human granulysin is provided as SEQ ID NO:1. The 31-50 peptide has the sequence, (SEQ ID NO:2):

| T | R | V | C | R | T | G | R | S | R | W | R | D | V | C | R | N | F | M | R |
|---|---|---|---|---|---|---|---|---|---|---|---|---|---|---|---|---|---|---|---|
| 31 | 32 | 33 | 34 | 35 | 36 | 37 | 38 | 39 | 40 | 41 | 42 | 43 | 44 | 45 | 46 | 47 | 48 | 49 | 50 |

In one embodiment, the peptide composition is a derivative of 31-50, or 42-51, which has been modified to increase hydrophobicity relative to the native peptide. Methods of increasing hydrophobicity include amino acid substitutions. Hydrophobic amino acid substitutions of interest include peptides comprising a substituted amino acid at position 44, e.g. substituting the val (V) for a more hydrophobic amino acid, e.g. M, F, W or C. 44W is exemplary, but those of skill in the art can readily substitute this position with other hydrophobic residues. Other residues that may be substituted with a hydrophobic amino acid as recited above are the arg (R) residues at positions 32, 35, 38, 40, 46 and 50; and the asp (N) at position 47. A preferred peptide comprises at least one amino acid substitution that increases the hydrophobicity of the peptide, and may comprise one, two three, four or more hydrophobic substitutions.

Peptides of interest may further comprise amino acid substitution(s) at naturally occurring cysteine residues, for example at one or more of positions 7, 34, 45 and 70 of the human granulysin sequence. Cysteine substitutions of particular interest include small polar or neutral amino acids, e.g. alanine, threonine, serine, glycine, etc. Such cysteine substitutions are known in the art, for example as taught by Wang et al., supra.; and by Ernst et al., supra.

In one embodiment of the invention the peptide comprises the sequence: SEQ ID NO:3 TRVSRTGRSRWRDWSRN-FMR or a biologically active fragment thereof.

The nucleic acid sequences encoding the above human granulysin polypeptides may be accessed from public databases or the sequence listing as previously cited. Identification of non-human granulysins is accomplished by conventional screening methods of DNA libraries or biological samples for DNA sequences having a high degree of similarity to known granulysin sequences.

As described above, the sequence of granulysin peptides may be altered in various ways known in the art to generate targeted changes in sequence. The sequence changes may be substitutions, insertions or deletions. Such alterations may be used to alter properties of the protein, by affecting the stability, specificity, etc. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp.15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated, where the polyethyleneoxy group provides for enhanced lifetime in the blood stream. The peptides may also be combined with other proteins, such as the Fc of an IgG isotype, which may be complement binding, with a toxin, such as ricin, abrin, diphtheria toxin, or the like, or with specific binding agents that allow targeting to specific moieties on a target cell.

The granulysin for use in the subject methods may be produced from eukaryotic or prokaryotic cells, or may be synthesized in vitro. Where the protein is produced by prokaryotic cells, it may be further processed by unfolding, e.g. heat denaturation, DTT reduction, etc. and may be further refolded, using methods known in the art.

Modifications of interest that do not alter primary sequence include chemical derivatization of polypeptides, e.g., acetylation, carboxylation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are peptides that have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In one embodiment of the invention, the antimicrobial peptide consists essentially of a polypeptide sequence of at least 10 amino acids in length and having a sequence within residues 31-50; or 42-51 of human granulysin, further comprising at least one hydrophobic amino acid substitution as described above. By "consisting essentially of" in the context of a polypeptide described herein, it is meant that the polypeptide is composed of the granulysin sequence, which sequence may be flanked by one or more amino acid or other residues that do not materially affect the basic characteristic(s) of the polypeptide.

The invention includes nucleic acids encoding the peptides of the invention. Granulysin coding sequences can be generated by methods known in the art, e.g. by in vitro synthesis, recombinant methods, etc. to provide a coding sequence to corresponds to a granulysin polypeptide that can serve as an intermediate in the production of the granulysin peptide. Using the known genetic code, one can produce a suitable coding sequence. Double or single stranded fragments can be obtained from the DNA sequence by chemically synthesizing oligonucleotides in accordance with conventional methods, by restriction enzyme digestion, by PCR amplification, etc.

Granulysin encoding nucleic acids can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Expression vectors may be used to introduce a granulysin coding sequence into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The nucleic acid may be introduced into tissues or host cells by any number of routes, including viral infection, microinjection, or fusion of vesicles. Jet injection may also be used for intramuscular administration, as described by Furth et al. (1992) Anal Biochem 205:365-368. The DNA may be coated onto gold microparticles, and delivered intradermally by a particle bombardment device, or "gene gun" as described in the literature (see, for example, Tang et al. (1992) Nature 356:152-154), where gold microprojectiles are coated with the stresscopin or DNA, then bombarded into skin cells.

Methods of Use

Formulations of granulysins are administered to a host suffering from an ongoing microbial infection or who faces exposure to a microbial infection. Administration may be topical, localized or systemic, depending on the specific microorganism. Generally the dosage will be sufficient to decrease the microbial population by at least about 50%, usually by at least 1 log, and may be by 2 or more logs. The compounds of the present invention are administered at a dosage that reduces the pathogen population while minimizing any side-effects. It is contemplated that the composition will be obtained and used under the guidance of a physician for in vivo use. Granulysin peptides are particularly useful for killing Propionibacterium acnes.

Granulysins are also useful for in vitro formulations to kill microbes, particularly where one does not wish to introduce quantities of conventional antibiotics. For example, granulysins may be added to animal and/or human food preparations, or to blood products intended for transfusion to reduce the risk of consequent bacterial or viral infection. This may be of particular interest since a common route of infection of *E. coli* and *L. monocytogenes* is the gastrointestinal tract. Granulysins may be included as an additive for in vitro cultures of cells, to prevent the overgrowth of microbes in tissue culture.

The susceptibility of a particular microbe or virus to killing or inhibition by granulysins may be determined by in vitro testing, as detailed in the experimental section. Typically a culture of the microbe is combined with granulysins at varying concentrations for a period of time sufficient to allow the protein to act, usually ranging from about one hour to one day. The viable microbes are then counted, and the level of killing determined. Two stage radial diffusion assay is a convenient alternative to determining the MIC or minimum inhibitory concentration of an antimicrobial agent.

Microbes of interest, but are not limited to, gram positive bacilli, e.g. *Propionibacterium* sp., e.g. *P. acnes; Clostridia* sp., e.g. *C. tetani, C. botulinum; Corynebacterium* sp., e.g. *C. diptheriae; Staphylococcus* sp., e.g. *S. aureus, S. epidermidis; Streptococcus* sp., e.g. *S. pyogenes, S. pneumoniae, S. agalactiae*. Gram negative bacteria include *Citrobacter* sp.; *Enterobacter* sp.; *Escherichia* sp., e.g. *E. coli; Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y enterocolitica; Francisells* sp.; *Pasturella* sp.; *Vibrio* sp., e.g. *V. cholerae, V. parahemolyticus; Campylobacter* sp., e.g. *C. jejuni; Haemophilus* sp., e.g. *H. influenzae, H. ducreyi; Bordetella* sp., e.g. *B. pertussis, B. bronchiseptica, B. parapertussis; Brucella* sp., *Neisseria* sp., e.g. *N. gonorrhoeae, N. meningitidis*, etc. Other bacteria include *Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Treponema* sp., e.g. *T. pallidum; Borrelia* sp., e.g. *B. burgdorferi; Leptospirae* sp.; *Rickettsia* sp., e.g. *R. rickeffsii, R. typhi; Chlamydia* sp., e.g. *C. trachomatis, C. pneumoniae, C. psittaci; Helicobacter* sp., e.g. *H. pylon*, etc.

Non baterial pathogens of interest include fungal and protozoan pathogens, e.g. *Plasmodia* sp., e.g. *P. falcipanum, Trypanosoma* sp., e.g. *T. brucei; shistosomes; Entaemoeba* sp., *Cryptococcus* sp., *Candida* sp, e.g. *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific granulysin peptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration.

Formulations of the granulysin peptides are administered to a host affected by various chronic or acute conditions involving inflammation. The compounds of the present invention are administered at a dosage that reduces inflammation while minimizing any side-effects. This invention includes methods for prevention or treatment of acute or chronic inflammation pain comprising administering to a patient in need thereof an effective dose of a granulysin peptide.

Conditions of interest include inflammatory musculoskeletal conditions in acute, subacute or chronic presentation. For example, the composition may be used in the treatment of both the early and late stages of inflammatory arthritis, as well as non-infectious inflammatory arthropathy such as rheumatoid arthritis, bursitis, tendinitis, soft tissue injuries, Sjogren's syndrome, systemic lupus erythematous, psoriatic arthritis, gout and other crystalline arthropathies, capsulitis, carpal tunnel syndrome, myositis, polymyalgia, rheumatica, synovitis and Reiter's syndrome. The compositions of this invention may also be used in the prevention or treatment of erosive osteoarthritis.

Inflammation involves capillary dilation, with accumulation of fluid and migration of phagocytic leukocytes, such as granulocytes and monocytes, to the site of injury or lesion. Inflammation is important in defending a host against a variety of infections, but can also have undesirable consequences in inflammatory disorders. Inflammatory conditions include autoimmune diseases; inflammation caused by bacterial and viral infection, including response to vaccination; local inflammation in response to trauma; graft rejection; graft v. host disease, and the like.

Furthermore, the compositions may be administered for dental applications. For example, the compositions of this invention are useful in preventing inflammation after tooth extraction or for treating various forms of gum disease. More specifically, after a periodontist performs gum surgery, an amount of the composition may be taken orally, or in the form of a liquid, gel or cream to be applied directly to the wound, or may be used to bathe the inflamed tissues as a rinse.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols. As such, administration of the compounds can be achieved in various ways, including oral, vaginal, buccal, rectal, parenteral, intraperitoneal, intradermal, transdermal, intratracheal, etc., administration. The granulysins may be systemic after administration or may be localized by the use of an implant or other formulation that acts to retain the active dose at the site of implantation.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral, vaginal or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing granulysins is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 µg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

Formulations with Other Active Agents

For use in the subject methods, granulysins may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Cytokines may also be included in a granulysin formulation, e.g. interferon γ, tumor necrosis factor α, interleukin 12, etc.

Antiviral agents, e.g. acyclovir, gancyclovir, etc. may also be included in granulysin formulations.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a granulysin formulation, e.g. interferon gamma., tumor necrosis factor .alpha., interleukin 12, etc.

As an alternative to antibiotics, granulysin may be formulated with perforin, or other agents that increase the ability of granulysin to act on intracellular organisms, e.g. *M. tb., C. trachomatis, R. ricketsii*, etc. Such agents may be perforin, granzymes, $CAPO_4$, etc. and will be added at a dose that is effective to increase granulysin killing of an intracellular pathogen by at least about 25%, usually at least about 50%.

Granulysin peptides may be formulated with anti-inflammatory drugs and herbal medicines. Herbal medicines of interest include, but not restricted to, active fractions from certain herbal preparations such as nettles (*Urtica dioica*) or turmeric (*Curcuma longa*); marine or terrestial animal products, e.g. bioactive lipids from *Pema canaliculus, Dromaius nova* hollandiae, etc. In addition, other known synergists, e.g. stable prostaglandin analogues such as misoprostol, etc., may potentiate the therapeutic effects.

Such compositions may include any variety of those drugs generally classified as nonsteroidal anti-inflammatory drugs (NSAIDs). By way of example, these drugs include ibuprofen, piroxicam, salicylate, aspirin, naproxen, indomethacin, diclofenac, or any mixture thereof. Also of interest are NSAIDs, such as fenoprofen calcium, nalfon, flurbiprofen, Ansaid, ibuprofen, ketoprofen, naproxen, anaprox, aflaxen, oxaprozin, diclofenac sodium, diclofenac potassium, cataflam, etodolac, indomethacin, ketorolac tromethamine, nabumetone, sulindac, tolmetin sodium, fenamates, meclofenamate sodium, mefenamic acid, piroxicam, salicylic acid, diflunisal, aspirin, oxyphenbutazone, and phenylbutazone.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Conventional antibiotics are currently used for skin infections. However, the increase in antibiotic-resistant strains of Gram-positive bacteria has hastened research for development of novel therapeutic agents. We have evidence that the body's own natural antimicrobial peptides may be useful therapeutic agents in the treatment of skin infections due to Gram-positive bacteria. Naturally occurring antibiotics are found in broad range of cell types including monocytes, granulocytes, and keratinocytes, and have been shown to have a broad spectrum of antimicrobial activity against bacterium, fungi, yeasts, and parasites. In addition to their ability to directly kill pathogens, antimicrobial peptides have also been shown to modulate host defense by a variety of mechanisms. In some circumstances, antimicrobial peptides may have pro-inflammatory activity while others may have anti-inflammatory effects. Thus as a group, antimicrobial peptides can either enhance or dampen the immune response and may be useful in the treatment of inflammatory skin diseases.

Granulysin is a 9 kDa basic (arginine-rich) protein and is a member of a larger group of proteins, referred to as saposin-like proteins (sphingolipid activator protein like protein=SAPLIP). This family has been highly conserved for almost a billion years, from amoebas to humans. Granulysin is part of a subset of SAPLIP family members with demonstrated antimicrobial activity. This family includes NK-lysin, isolated from pig intestines, and amoebapores, used by amoebas to kill bacterial prey. Experiments performed in our laboratory led to the discovery that granulysin has a wide range of antimicrobial activity against bacteria, parasites and fungi. We have synthesized a shorter granulysin peptide 20 amino acid in length and tested for antimicrobial activity. Further modification of this peptide was done by substituting a more hydrophobic amino acid residue, tryptophan at position 44, and tested for antimicrobial activity.

Figure 1:
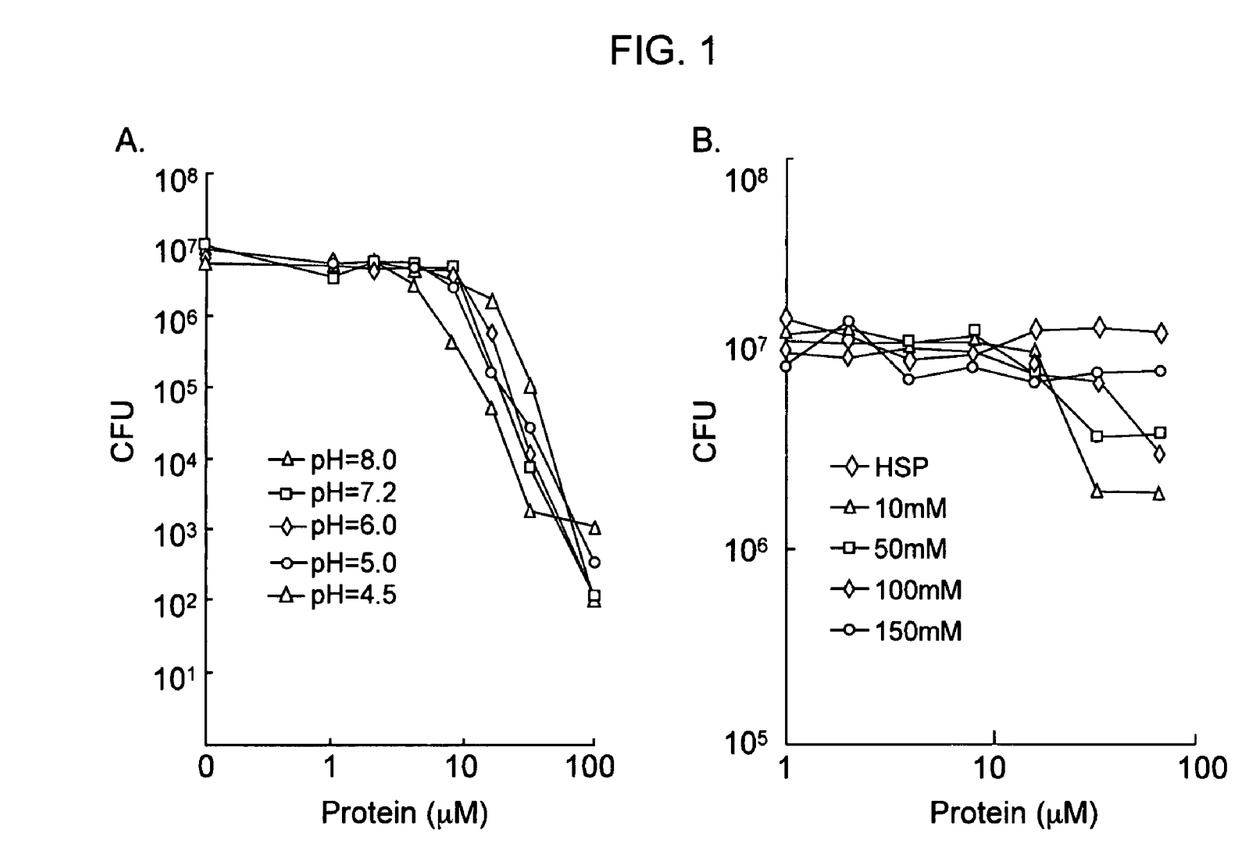
FIG. 1A-B. Analysis of the effect of pH and ionic interaction between granulysin and *P. acnes*.
Figure 2:
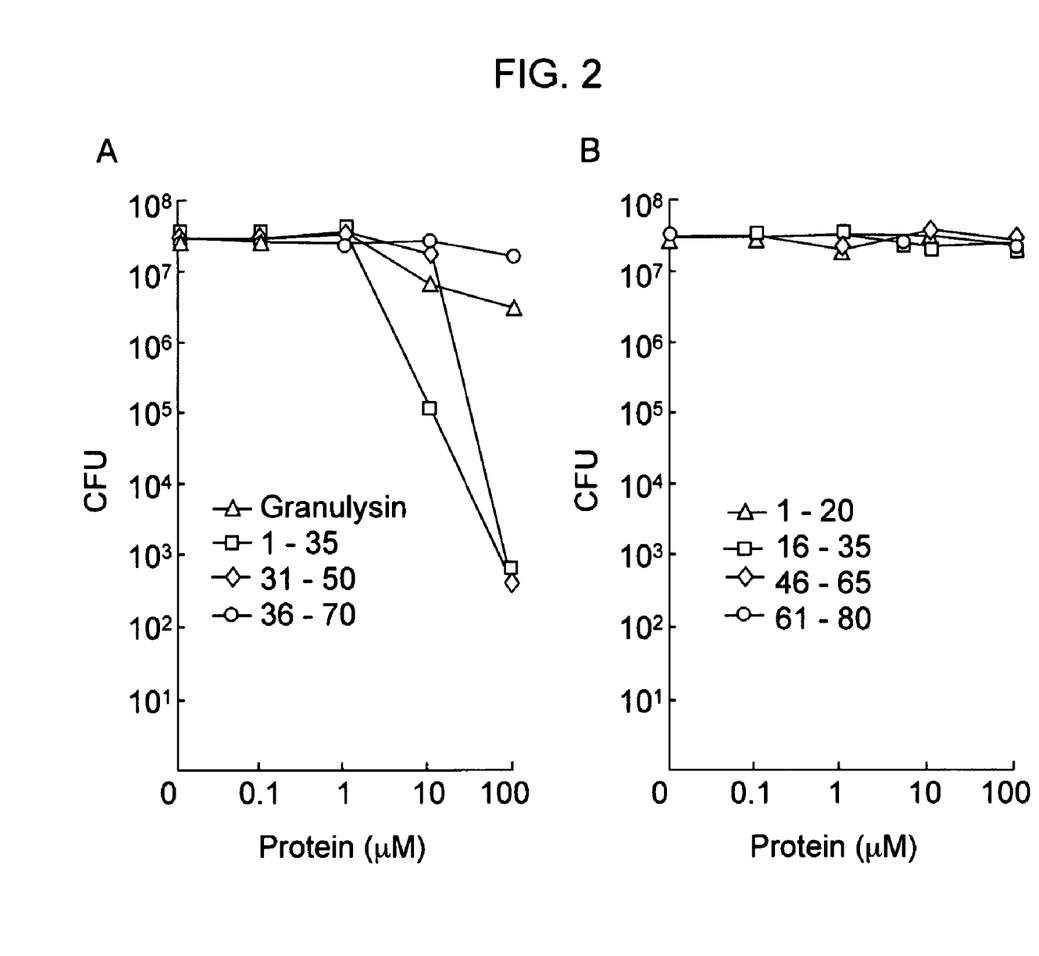
FIG. 2A-B. Antimicrobial activity of granulysin and granulysin peptides.
Figure 3:
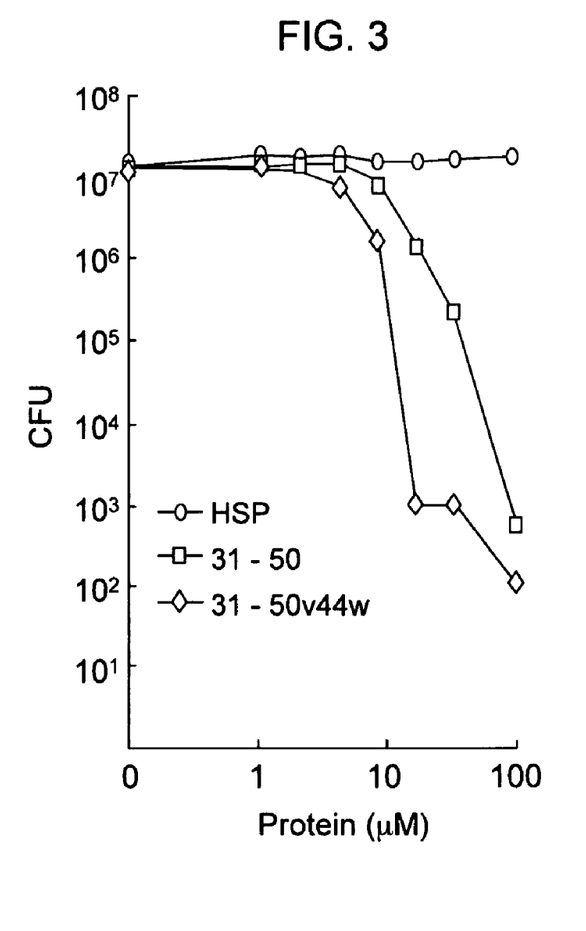
FIG. 3. Activity of synthetic granulysin peptides.
Figure 4:
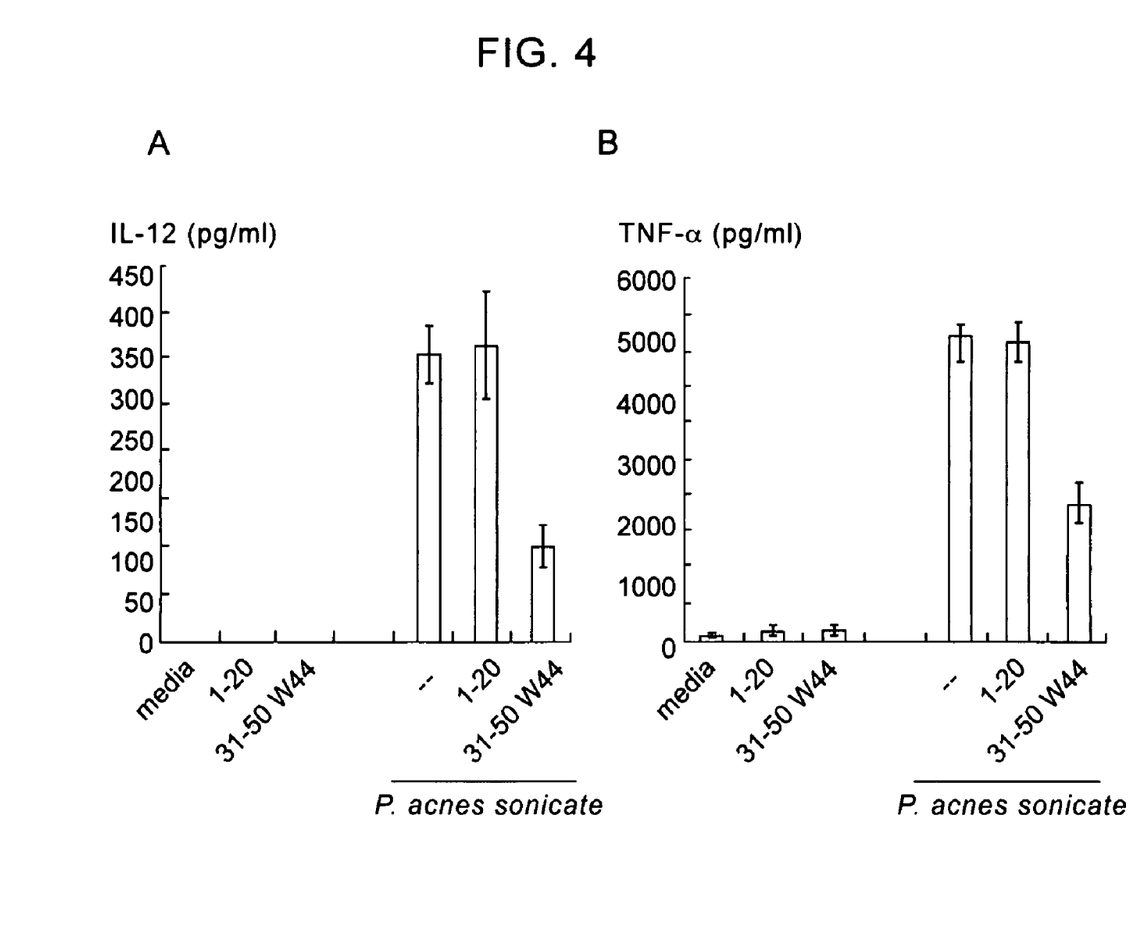
FIG. 4A-B. Anti-inflammatory activity of synthetic granulysin peptides.

We have demonstrated that the 9 kD granulysin is effective at killing Propionibacterium acnes, a Gram-positive bacteria that plays a role in the pathogenesis of acne vulgaris. The antimicrobial activity of granulysin has been tested at various pH (FIG. 1a) and inonic concentration (FIG. 1b) settings for optimization of killing. We have synthesized short synthetic granulysin peptides and found that granulysin peptides containing alpha helical-loop-helical secondary structures are antimicrobial against $P.$ acnes (FIG. 2a). In contrast synthetic granulysin peptides without the alpha helical-loop-helical secondary structure do not have antimicrobial activity against $P.$ acnes (FIG. 2b). In particular, granulysin peptide containing amino acids #31-50 was found to be effective at killing $P.$ acnes. We then calculated the hydrophobic moment for granulysin peptides and amino acid residues in granulysin peptides were manipulated to generate similar peptides with greater hydrophobic moments, i.e. with a greater predicted tendency to form alpha helices. We identified a modified granulysin peptide #31-50(W44) which demonstrated even a greater antimicrobial activity against $P.$ acnes then the non-modified granulysin peptide #31-50 (FIG. 3). Furthermore, we found that the synthetic granulysin peptide #31-50(W44) also has anti-inflammatory activity and is able to inhibit IL-12 (FIG. 4a) and TNF-α (FIG. 4b) production by monocytes. In addition, we have tested all our granulysin peptides for their cytotoxic activity against eukaryotic cells and found that these peptides are not toxic to human monocytes and keratinocytes.

The endogenous antimicrobial peptides offer two critical advantages over conventional therapy because first they have a broad spectrum of antimicrobial activity. Second, these, peptides are directly microbicidal and not dependent on interfering with the microbe's survival machinery such as cell wall or RNA synthesis. Instead, the endogenous peptides form multimers on the surface of the microbes, leading to pore formation, membrane rupture, and cell death. Because antimicrobial peptides target negatively charged lipids that are the product of complex biosynthetic pathways, rather than a single genetically-encoded enzyme, the development of microbes resistant to the peptides would likely be less than with the conventional antibiotics currently in use.

The technology we have developed is marketable as a novel antimicrobial therapy for skin infection due to Gram-positive organisms. In addition, our technology has great potential in combating a variety of different infectious diseases caused by viruses, Gram-negative bacteria, yeast, and fungi, and cancers. Furthermore, the modified granulysin peptide #31-50(W44) also has anti-inflammatory property and therefore can be used for treatment of inflammatory diseases. Given that our modified peptide is small in size, cutaneous delivery will be easier to accomplish and treatments can be targeted to skin.

The development of effective antimicrobial peptide provides a new therapeutic modality for the treatment of cutaneous infection and inflammation in particular those caused by Gram-positive bacteria.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating cutaneous microbial infection, the method comprising: administering an effective dose of a granulysin peptide, SEQ ID NO:2, wherein SEQ ID NO:2 comprises a hydrophobic amino acid substitution at position 44.

2. The method according to claim 1, wherein said microbial organism is *Propionibacterium acnes*.

* * * * *